US012728133B2

(12) United States Patent
Guimberteau et al.

(10) Patent No.: US 12,728,133 B2
(45) Date of Patent: Sep. 8, 2026

(54) CONTROLLED-RELEASE PROGESTERONE COMPOSITIONS AND USES THEREOF

(71) Applicant: CEVA SANTE ANIMALE, Libourne (FR)

(72) Inventors: Florence Guimberteau, Libourne (FR); Sandrine Lacoste, Libourne (FR)

(73) Assignee: CEVA SANTE ANIMALE, Libourne (FR)

( * ) Notice: Subject to any disclaimer, the term of this patent is extended or adjusted under 35 U.S.C. 154(b) by 392 days.

(21) Appl. No.: 18/553,593

(22) PCT Filed: Apr. 1, 2022

(86) PCT No.: PCT/EP2022/058747

§ 371 (c)(1),
(2) Date: Oct. 2, 2023

(87) PCT Pub. No.: WO2022/207902

PCT Pub. Date: Oct. 6, 2022

(65) Prior Publication Data

US 2024/0180928 A1 Jun. 6, 2024

(30) Foreign Application Priority Data

Apr. 1, 2021 (EP) .................................... 21305424

(51) Int. Cl.
*A61K 31/57* (2006.01)
*A61K 9/00* (2006.01)
*A61K 47/32* (2006.01)

(52) U.S. Cl.
CPC ............ *A61K 31/57* (2013.01); *A61K 9/0036* (2013.01); *A61K 9/0043* (2013.01); *A61K 47/32* (2013.01)

(58) Field of Classification Search
CPC ........ A61K 31/57; A61K 47/06; A61K 47/10; A61P 15/00
USPC ................................................. 514/169, 171
See application file for complete search history.

(56) References Cited

U.S. PATENT DOCUMENTS

2010/0040671 A1 2/2010 Ahmed et al.
2019/0290474 A1 9/2019 Simpson et al.

FOREIGN PATENT DOCUMENTS

EA 201170199 A1 8/2011

OTHER PUBLICATIONS

International Search Report and Written Opinion in International Application No. PCT/EP2022/058747 with partial translation, 11 pages. Jul. 25, 2022.
Vandelli et al., "Analysis of Release Data in the Evaluation of the Physical State of Progesterone in Matrix Systems", J. Microencapsulation, vol. 10, No. 1, pp. 55-65. 1993.

*Primary Examiner* — Charanjit Aulakh
(74) *Attorney, Agent, or Firm* — Heslin Rothenberg Farley & Mesiti P.C.

(57) ABSTRACT

The present invention relates to a composition comprising between 35 and 55% by weight of a polymer matrix comprising a thermoplastic polymer having a Shore A hardness of between 20 and 100 as measured by a Type A durometer according to the ASTM D2240 standard and a melting point of between 40 and 200° C.; and between 30 and 55% by weight of progesterone relative to the total weight of the composition. The invention further relates to the use of such compositions to synchronise the estrus of a group of non-human mammals, preferably a group of bovines.

20 Claims, 5 Drawing Sheets

CONTROLLED-RELEASE PROGESTERONE COMPOSITIONS AND USES THEREOF

CROSS REFERENCE TO RELATED APPLICATIONS

Figure 1:
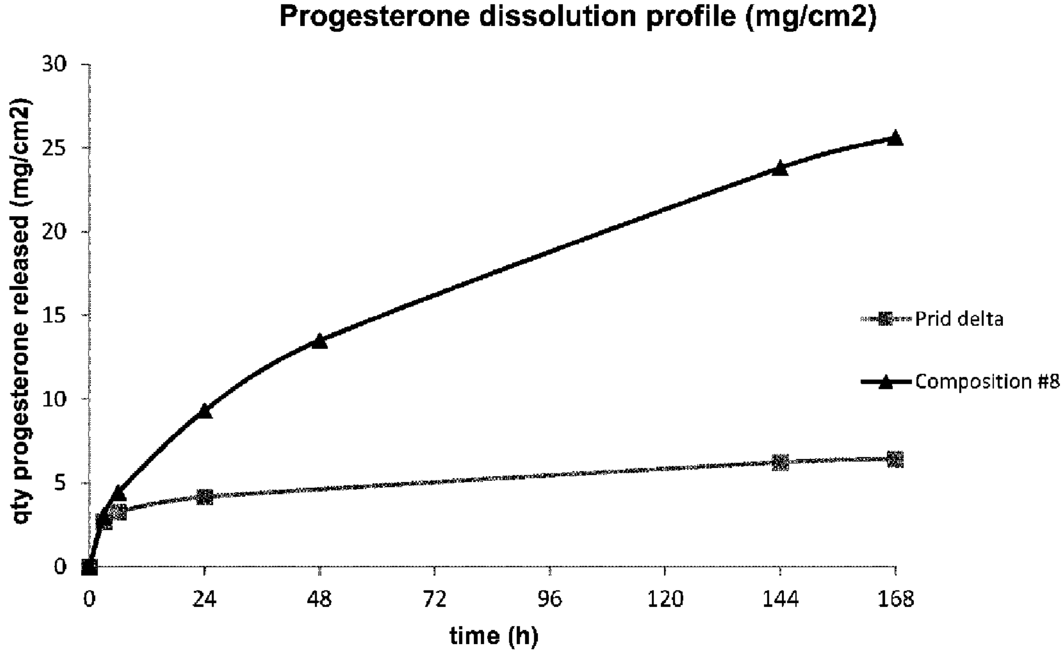

This application is a U.S. National Phase filing under 35 U.S.C. § 371 of International Application PCT/EP2022/058747, filed Apr. 1, 2022, and published as WO2022/207902A1 on Oct. 6, 2022. PCT/EP2022/058747 claims priority from European application number 21305424.0, filed Apr. 1, 2021. The entire contents of each of these prior applications are hereby incorporated herein by reference.

SUBJECT OF THE INVENTION

The present invention relates to the field of polymer compositions for controllably releasing drugs, and more specifically progesterone, in a mammal.

TECHNOLOGICAL BACKGROUND OF THE INVENTION

Progesterone is a natural steroidal hormone secreted by the cells of the corpus luteum of the ovaries and the placenta. It is involved in pregnancy, embryogenesis, and the menstrual cycle of numerous species of mammals.

Progesterone is also commonly administered in mammals, in particular in cattle, to synchronize estrous in order to control and harmonize sexual cycles of females. Estrous synchronization facilitates artificial insemination by relieving the inseminator of certain constraints related to the detection of estrous and thus has numerous advantages in terms of saving time and costs. More specifically, the advantages of estrous synchronization are in particular the elimination of the monitoring of the estrous of the females and the constitution of batches of homogeneous animals which make it possible to carry out the artificial insemination in several females at a fixed and planned date. This artificial insemination date makes it possible to group the calvings and thus facilitate their monitoring.

Various polymer compositions for controlling the release of progesterone in non-human mammals have thus been developed. For example, the company JUROX PTY LTD describes, in international patent application WO 2017/117627, polymer compositions comprising an amount by weight of progesterone between 5 and 15% by weight relative to the total weight of the composition. These polymer compositions are more particularly used in intravaginal devices. The company Ceva Santé Animale has also developed bovine vaginal diffusion systems for progesterone, such as Prid delta systems comprising a polymer composition having a surface area of 170 $cm^2$, wherein progesterone is present in an amount of 11% by weight, relative to the total weight of the composition, thus corresponding to a ratio by weight of progesterone on the polymer matrix of 0.12 and to an area density of progesterone in the polymer matrix of 9.12 $mg/cm^2$.

However, these polymer compositions comprising a relatively low amount of progesterone (less than 15% by weight relative to the total weight of the composition) need to be in contact with a large mucosal surface to obtain an effective diffusion profile. These polymer compositions that are not very concentrated with progesterone are thus better suited to large-sized devices that have a large surface area of contact with the mucous membranes. Indeed, polymer compositions that are not very concentrated with progesterone would be less suitable for compact devices of small size, having a minimum contact surface with the mucous membranes, insofar as the amount of progesterone could be insufficient for an efficacious biological effect.

There is thus currently a need to develop and provide novel polymer compositions concentrated with progesterone allowing an effective, continuous, extended release.

SUMMARY OF THE INVENTION

In this context, the inventors have developed compositions with controlled release of progesterone comprising a polymer matrix wherein a relatively concentrated amount of progesterone of at least 30% by weight relative to the total weight of the composition is impregnated. Such polymer compositions have satisfactory progesterone diffusion profiles comparable to those observed with the compositions comprising a lesser amount of progesterone, at a concentration of 5-15% by weight relative to the total weight of the composition. The polymer compositions according to the invention therefore make it possible to release, in a controlled and extended manner over time, an effective amount of progesterone on a small mucous membrane surface. The polymer compositions according to the invention also have a certain flexibility. In light of their properties and advantages, the polymer compositions according to the invention can be used in compact and small devices, which are more comfortable for the mammal, thus improving its well-being.

The present invention therefore relates to a composition, preferably with controlled release of progesterone, comprising:

- between 35 and 55% by weight of a polymer matrix comprising a thermoplastic polymer having a Shore A hardness of between 20 and 100 as measured by a Type A durometer according to the ASTM D2240 standard and a melting point of between 40 and 200° C.; and
- between 30% and 55%, preferably between 35% and 55%, by weight of progesterone, relative to the total weight of the composition.

The invention further relates to a composition comprising:

- a polymer matrix comprising a thermoplastic polymer having a Shore A hardness of between 20 and 100 as measured by a Type A durometer according to the ASTM D2240 standard and a melting point of between 40 and 200° C.; and
- progesterone, wherein the ratio by weight of progesterone to the polymer matrix is between 0.5 and 2, preferably between 0.54 and 1.57, and even more preferably 1.00 or 1.28.

The invention also relates to a composition comprising:

- a polymer matrix comprising a thermoplastic polymer having a Shore A hardness of between 20 and 100 as measured by a Type A durometer according to the ASTM D2240 standard and a melting point of between 40 and 200° C.; and
- progesterone, wherein the area density of progesterone in the polymer matrix is between 20 and 100 $mg/cm^2$, preferably between 25 and 80 $mg/cm^2$.

In particular, the thermoplastic polymer is chosen from a thermoplastic polymer of the EVA type, and a thermoplastic elastomer polymer (TPE).

Preferably, the thermoplastic polymer of the EVA type is an ethylene-vinyl acetate copolymer comprising 18%, 28%, or 40%, preferably 40% by weight of vinyl acetate monomer relative to the total weight of ethylene-vinyl acetate copolymer.

Preferably, the thermoplastic elastomer polymer (TPE) is selected from a styrene block-based thermoplastic elastomer polymer (TPE-S), and a polyurethane thermoplastic elastomer polymer (TPE-U).

According to a more preferred embodiment, the thermoplastic elastomer polymer (TPE) is a styrene block-based thermoplastic elastomer polymer (TPE-S) chosen from a block copolymer of polystyrene-polybutadiene-polystyrene (SBS), a block copolymer of polystyrene-polyene-polystyrene (SIS), a block copolymer of polystyrene-polyisobutylene-polystyrene (SIBS), a block copolymer of polystyrene-poly(ethylene-propylene)-polystyrene (SEPS), a block copolymer of polystyrene-poly(ethylene-propylene) (SEP), a block copolymer of polystyrene-poly(ethylene-butylene)-polystyrene (SEBS), a block copolymer of poly-α-methylstyrene-poly(butadiene-isoprene)-α-methylstyrene, a block copolymer of polydimethylsiloxane-styrene, a graft block copolymer of polystyrene-polybutadiene, a graft block copolymer of polystyrene-poly(ethylene oxide), a block copolymer of poly[styrene-per-dimethylsiloxane), and a block copolymer of polyisobutylene polystyrene (PIB-PS). According to an even more preferred embodiment, the thermoplastic elastomer polymer (TPE) is a formulation comprising a block copolymer of polystyrene-poly(ethylene-butylene)-polystyrene (SEBS), paraffin oil, and polypropylene.

A particular object of the invention is a composition as described above further comprising between 5 and 35% by weight of a pore-forming agent and/or of a swelling agent, relative to the total weight of the composition.

According to a particular embodiment, the pore-forming agent is polyethylene glycol, having preferably a molecular weight between 1500 and 8000 g/mol, between 2000 and 6000 g/mol, and even more preferably 4000 g/mol.

According to another particular embodiment, the swelling agent is polyethylene oxide.

A preferred composition of the invention comprises:

- between 35 and 55%, preferably 35% by weight of ethylene-vinyl acetate copolymer,
- between 10 and 30%, preferably 20% by weight of polyethylene glycol, and
- between 35 and 55%, preferably 45% by weight of progesterone, relative to the total weight of the composition.

Another preferred composition of the invention comprises:

- between 35 and 55%, preferably 50% by weight of a formulation comprising a polystyrene-poly(ethylene-butylene)-polystyrene block copolymer, paraffin oil, and polypropylene; and
- between 30 and 55%, preferably between 35 and 55%, and even more preferably 50% by weight of progesterone, relative to the total weight of the composition.

According to a preferred embodiment of the invention, the composition as described in the present application is a veterinary composition. Preferably, said composition is applied to a bovine, a caprine, a sheep, and a pig, and even more preferably to a bovine.

Another object of the invention relates to a composition as described in the present application for its use to synchronize the estrous of a group of non-human mammals, preferably a group of bovines, goats, sheep, or pigs.

According to a particular embodiment of the invention, the composition is administered mucosally, preferably nasally or intravaginally.

An additional object of the invention relates to a device for controlled release of an active ingredient comprising a composition as defined in the present application. Preferably, the device is a nasal or intravaginal device.

LEGEND FOR THE FIGURES

FIG. 1: Amount of progesterone released per unit area (mg/cm$^2$) with composition #8 according to the invention, and the composition Prid delta.

Figure 2:
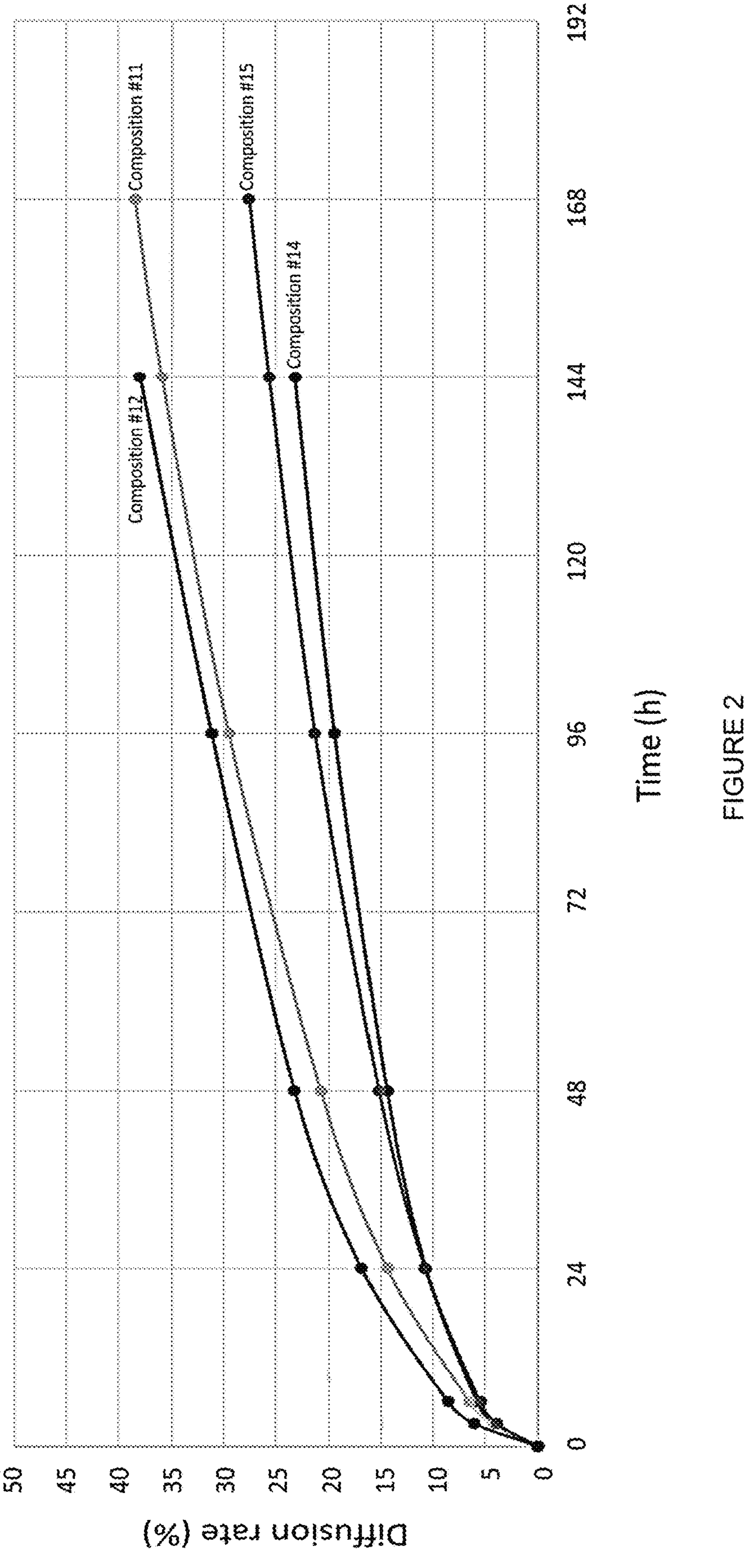
Figure 3:
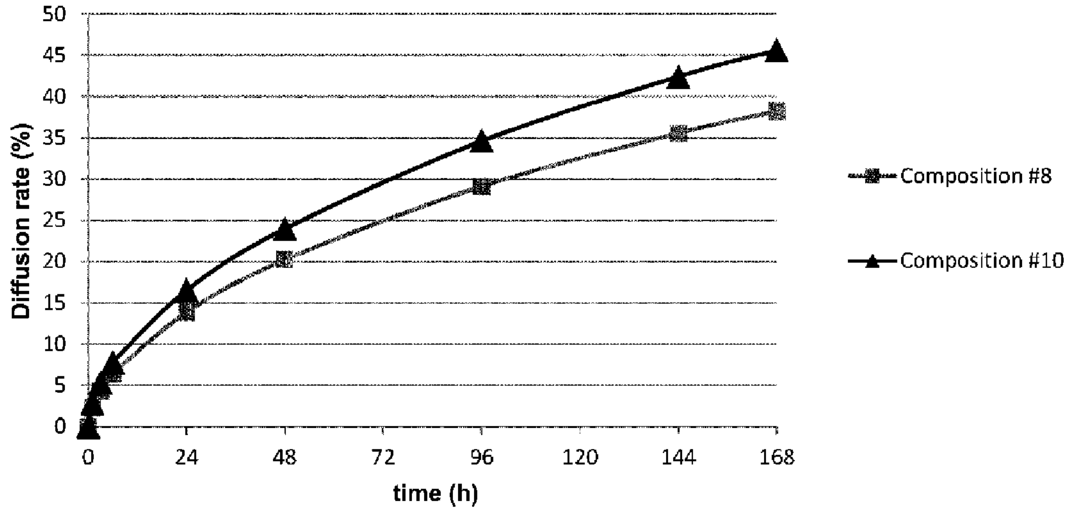
Figure 4:
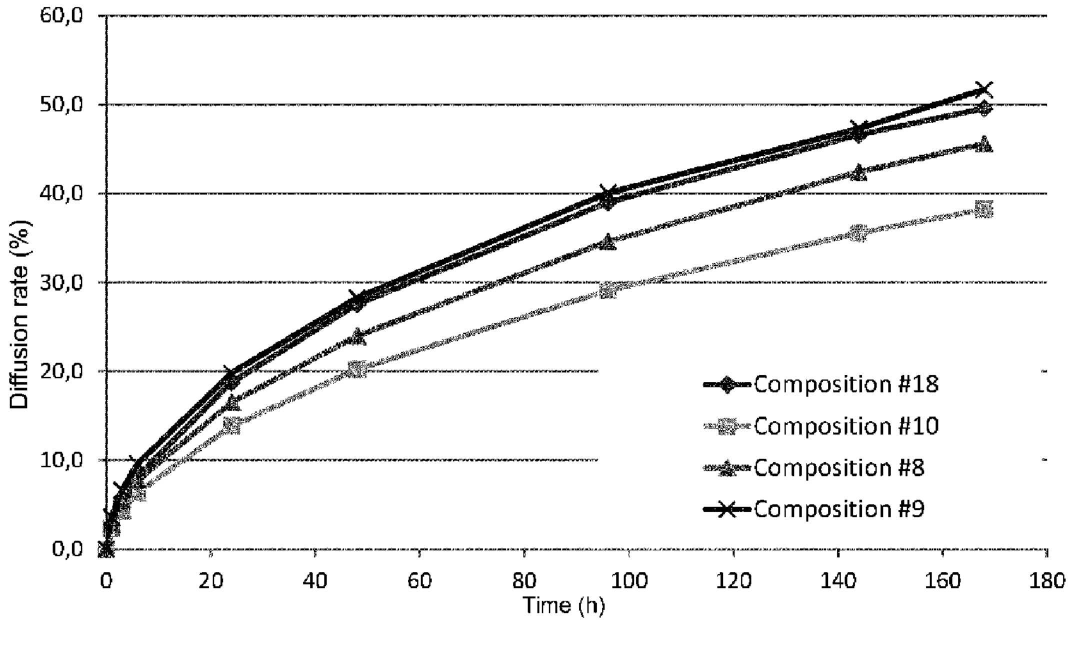

FIG. 2-4: Influence of a pore-forming or swelling agent Progesterone diffusion profile (%) with compositions #14, #11, #15, and #12 according to the invention (FIG. 2). Progesterone diffusion profile (%) with compositions #8, and #10 according to the invention (FIG. 3). Progesterone diffusion profile (%) with compositions #18, #10, #8, and #9 according to the invention (FIG. 4).

FIGS. 5A-5D: Representation of devices comprising a composition according to the invention.

DETAILED DESCRIPTION OF THE INVENTION

The present invention provides a polymer composition concentrated with progesterone ensuring controlled release of this pharmaceutical active ingredient in the mammal wherein the composition is applied. More particularly, the polymer compositions according to the invention have a ratio by weight of progesterone on the polymer matrix significantly greater (5 to 15 times) than that of the controlled-release compositions of progesterone in common use.

"Controlled release of an active ingredient" refers to extended, continuous release over time. More particularly, a controlled-release active ingredient diffuses more slowly and longer in the body for better absorption, and therefore better biological effect.

The present invention therefore relates to a composition comprising:

- between 35 and 55% by weight of a polymer matrix comprising a thermoplastic polymer having a Shore A hardness of between 20 and 100 as measured by a Type A durometer according to the ASTM D2240 standard and a melting point of between 40 and 200° C.; and
- between 30% and 55%, preferably between 35% and 55%, by weight of progesterone, relative to the total weight of the composition.

The invention further relates to a composition comprising:

- a polymer matrix comprising a thermoplastic polymer having a Shore A hardness of between 20 and 100 as measured by a Type A durometer according to the ASTM D2240 standard and a melting point of between 40 and 200° C.; and
- progesterone, wherein the ratio by weight of progesterone to the polymer matrix is between 0.5 and 2, preferably between 0.54 and 1.57, and even more preferably 1.00 or 1.28.

According to a particular embodiment, the ratio by weight of progesterone to the polymer matrix is between 0.5 and 1.6, preferably between 0.54 and 1.57, between 0.60 and 1.50, between 0.70 and 1.40, between 0.80 and 1.30, between 0.90 and 1.30, between 0.95 and 1.30. According to a preferred embodiment, the ratio by weight of progesterone to the polymer matrix is 1.00 or 1.28.

The invention further relates to a composition comprising:

- a polymer matrix comprising a thermoplastic polymer having a Shore A hardness of between 20 and 100 as measured by a Type A durometer according to the ASTM D2240 standard and a melting point of between 40 and 200° C.; and progesterone, wherein the area density of progesterone in the polymer matrix is between 20 and 100 mg/cm$^2$, preferably between 25 and 80 mg/cm$^2$.

According to a particular embodiment, the area density of progesterone in the polymer matrix is between 20 and 100 mg/cm$^2$, preferably between 25 and 80 mg/cm$^2$, between 50 and 67 mg/cm$^2$ and is even more preferably about 29.85, about 43.48, about 50.00, about 56.25 mg/cm$^2$, and about 66 or 67 mg/cm$^2$.

The term "about" will be understood by a person skilled in the art and may vary to some extent depending on the context wherein it is used. Should some uses of this term not be clear to a person skilled in the art on the basis of the context, "about" means 20% greater or less than, preferably 10% greater or less than, the particular term.

As used herein, the term "comprises", "comprise" or "comprising" (and other comparable terms, for example, "containing" and "including") is "open-ended" and may be generally interpreted such that all the features mentioned and all optional, additional and features not specified are included. According to specific embodiments, it may also be interpreted as the expression "consisting essentially of" where the specified features and any optional, additional, unspecified features that do not materially affect the basic and novel features of the claimed invention are included, or the expression "consisting in" when only the specified features are included, unless otherwise indicated.

More specifically according to the invention, progesterone is impregnated into the polymer matrix. In the context of the present invention, the term "impregnated" also includes the terms "mixed", "integrated", "incorporated", "combined", "fused", and "amalgamated". Thus, the composition comprises a polymer matrix comprising a thermoplastic polymer having a Shore A hardness of between 20 and 100 as measured by a type A durometer according to the ASTM D2240 standard and a melting point of between 40 and 200° C., wherein progesterone is impregnated into the polymer matrix.

"Thermoplastic" material is understood to mean a material that can repeatedly be softened by heating and hardened by cooling. In the case of polymers, it is said that the polymerization of a thermoplastic material is reversible.

According to the invention, the polymer matrix comprises a thermoplastic polymer having a Shore A hardness of between 20 and 100 as measured by a type A durometer according to the standard ASTM D2240. Preferably, the thermoplastic polymer has a Shore A hardness of between 20 and 90, between 25 and 100, between 30 and 100, between 40 and 100, and even more preferably, the thermoplastic polymer has a Shore A hardness of 40.

The Shore hardness scale makes it possible to measure the hardness of the materials. There are no fewer than twelve existing Shore measurement scales, and the most common are the A scales for soft materials and D for hard materials. The hardness measurement method established by the ASTM D2240 standard makes it possible to measure the depth of an indentation created in a material to be characterized using an established force and a standardized indentation head. The depth is proportional to the hardness and ductility of the material as well as the geometry of the indentation head used. The ASTM D2240 standard consists of pressing the indentation head onto the material to be characterized and the hardness is directly read on the scale of the apparatus, such as a type A durometer for soft thermoplastic polymers.

According to the invention, the polymer matrix comprises a thermoplastic polymer having a melting point of between 40 and 200° C. Preferably, the thermoplastic polymer has a melting point of between 40 and 135° C., and even more preferably of 44° C.

The melting point or the melting temperature of a polymer is the temperature at which it changes from the rubbery state in the liquid or viscous state. The melting point of a polymer can be determined by various techniques known to a person skilled in the art, such as direct detection by visual observation with a capillary tube, detection with a polarizing microscope, and thermal analysis techniques, such as, for example, thermomechanical analysis, differential thermal analysis, and differential scanning calorimetry. More particularly, the thermoplastic polymer is chosen from a thermoplastic polymer of the EVA type, and a thermoplastic elastomer polymer (TPE).

The thermoplastic polymers of the EVA type are derived from the copolymerization of ethylene with vinyl acetate. There are several types of thermoplastic EVA polymers which differ by the proportion by weight of the vinyl acetate monomer relative to the total weight of the polymer (ethylene-vinyl acetate copolymer). For example, EVA 18 comprises 18% by weight of vinyl acetate monomer, relative to the total weight of ethylene-vinyl acetate copolymer. EVA 28 comprises 28% by weight of vinyl acetate monomer, relative to the total weight of ethylene-vinyl acetate copolymer. EVA 40 comprises 40% by weight of vinyl acetate monomer, relative to the total weight of ethylene-vinyl acetate copolymer. The thermoplastic polymers of the EVA type are generally hydrophobic and transparent. They have good chemical resistance and good impact resistance. They also have a high coefficient of friction and good adhesive properties.

In a preferred embodiment, the thermoplastic polymer of the EVA type is an ethylene-vinyl acetate copolymer comprising 18%, 28%, or 40% by weight of vinyl acetate monomer relative to the total weight of ethylene-vinyl acetate copolymer. In an even more preferred embodiment, the thermoplastic polymer of the EVA type is an ethylene-vinyl acetate copolymer comprising 40% by weight of vinyl acetate monomer relative to the total weight of ethylene-vinyl acetate copolymer. Thus, a preferred thermoplastic polymer of the EVA type is an EVA 18, EVA 28, or EVA 40 polymer. An even more preferred thermoplastic polymer of the EVA type is an EVA 40 polymer.

thermoplastic elastomer polymers (TPE) are a (often block) copolymer family that combine the elastic properties of elastomers and thermoplasticity.

"Elastomeric" polymer is understood to mean a polymer capable of regaining its shape after deformation. Thermoplastic elastomers are therefore heterogeneous polymers composed of regions of thermoplastic polymer material and of regions of elastomeric polymer material. The term "region" is used to describe a zone of a material that contains polymer chains of an elastomeric or thermoplastic nature. Preferably, the thermoplastic elastomer polymers (TPE) according to the invention comprise monomers or blocks of monomers which are of thermoplastic nature and blocks of monomers which are of elastomeric nature.

Thermoplastic elastomers (TPE) or block copolymers of thermoplastic monomers and of elastomeric monomers can be classified into different categories as a function of the nature and proportion of monomer. Without limitation, thermoplastic elastomer polymers include thermoplastic polymers based on styrene blocks (TPE-S), thermoplastic elastomer polymers based on polyester blocks (TPE-E), polyurethane elastomer thermoplastic polymers (TPE-U), thermoplastic elastomer polymers based on amide blocks (TPE-A), vulcanized thermoplastic polymers (TPE-V), and thermoplastic olefins (TPE-O).

Styrene block-based thermoplastic elastomer polymers (TPE-S) are, for example, chosen from a block copolymer of polystyrene-polybutadiene-polystyrene (SBS), a block copolymer of polystyrene-polyene-polystyrene (SIS), a block copolymer of polystyrene-polyisobutylene-polystyrene (SIBS), a block copolymer of polystyrene-poly(ethylene-propylene)-polystyrene (SEPS), a block copolymer of polystyrene-poly(ethylene-propylene) (SEP), a block copolymer of polystyrene-poly(ethylene-butylene)-polystyrene (SEBS), a block copolymer of poly-α-methylstyrene-poly (butadiene-isoprene)-α-methylstyrene, a block copolymer of polydimethylsiloxane-styrene, a graft block copolymer of polystyrene-polybutadiene, a graft block copolymer of polystyrene-poly(ethylene oxide), a block copolymer of poly [styrene-per-dimethylsiloxane), and a block copolymer of polyisobutylene polystyrene (PIB-PS).

Polyurethane thermoplastic elastomer polymers (TPE-U) are thermoplastic elastomer polymers based on isocyanate blocks.

Preferably, a thermoplastic elastomer polymer (TPE) is a styrene block-based thermoplastic elastomer polymer (TPE-S), and a polyurethane thermoplastic elastomer polymer (TPE-U).

Preferably, the thermoplastic elastomer polymer is a styrene block-based thermoplastic elastomer polymer (TPE-S). More particularly, styrene block-based thermoplastic elastomer polymers (TPE-S) are chosen from a block copolymer of polystyrene-polybutadiene-polystyrene (SBS), a block copolymer of polystyrene-polyene-polystyrene (SIS), a block copolymer of polystyrene-polyisobutylene-polystyrene (SIBS), a block copolymer of polystyrene-poly(ethylene-propylene)-polystyrene (SEPS), a block copolymer of polystyrene-poly(ethylene-propylene) (SEP), a block copolymer of polystyrene-poly(ethylene-butylene)-polystyrene (SEBS), a block copolymer of poly-α-methylstyrene-poly (butadiene-isoprene)-α-methylstyrene, a block copolymer of polydimethylsiloxane-styrene, a graft block copolymer of polystyrene-polybutadiene, a graft block copolymer of polystyrene-poly(ethylene oxide), a block copolymer of poly [styrene-per-dimethylsiloxane), and a block copolymer of polyisobutylene polystyrene (PIB-PS). According to an even more preferred embodiment, a styrene block-based thermoplastic elastomer polymer (TPE-S) is a block copolymer of polystyrene-poly(ethylene-butylene)-polystyrene (SEBS).

The thermoplastic elastomers (TPEs) described above can be in the form of a mixture in the compositions of the invention. The thermoplastic elastomers (TPEs) described above can also be formulated in the presence of other types of polymers such as polyethylene or polypropylene, and in the presence of excipient. A polymeric formulation suitable for the compositions of the invention is the commercial formulation Medioprene® from the company HEXPOL TPE, which comprises a block copolymer of polystyrene-poly(ethylene-butylene)-polystyrene (SEBS), paraffin oil, and polypropylene.

According to an even more advantageous embodiment, the styrene block-based thermoplastic elastomer polymer (TPE-S) is a formulation comprising a block copolymer of polystyrene-poly(ethylene-butylene)-polystyrene (SEBS), paraffin oil, and polypropylene.

A preferred composition of the invention comprises:

- between 35 and 55%, preferably 50% by weight of a formulation comprising a polystyrene-poly(ethylene-butylene)-polystyrene block copolymer, paraffin oil, and polypropylene; and
- between 30 and 55%, preferably between 35 and 55%, and even more preferably 50% by weight of progesterone, relative to the total weight of the composition.

According to one particular aspect of the invention, the composition further comprises a pore-forming agent and/or a swelling agent, preferably in a proportion of between 5 and 35% by weight, relative to the total weight of the composition. These agents make it possible to better control the release of progesterone of the polymer matrix and to improve the profile of progesterone diffusion in order to obtain an improved biological effect.

A pore-forming agent may be a polyethylene glycol, preferably having a molecular weight of between 1500 and 8000 g/mol, between 2000 and 6000 g/mol, and even more preferably 4000 g/mol, a polyvinyl alcohol, a polyvinylpyrrolidone, preferably having a low molecular weight such as polyvinylpyrrolidones K12 to K30, a sugar such as sucrose or lactose, or a surfactant, preferably nonionic.

A swelling agent may be a polyethylene oxide, a polyvinylpyrrolidone, preferably having a high molecular weight such as polyvinylpyrrolidone K90, a crospovidone, a carbomer, sodium carboxymethyl cellulose, sodium starch glycolate, cellulose derivatives such as hydroxypropylmethylcellulose and methylcellulose, or hydrocolloids such as alginates, chitosan, or pectin.

A preferred object according to the invention is a composition as described above further comprising between 5 and 35% by weight of a pore-forming agent and/or of a swelling agent, relative to the total weight of the composition.

According to a preferred embodiment, the pore-forming agent is polyethylene glycol. In particular, polyethylene glycol has a molecular weight between 1500 and 8000 g/mol, preferably between 2000 and 6000 g/mol, and even more preferably 4000 g/mol.

According to another preferred embodiment, the pore-forming agent is polyvinylpyrrolidone. Particularly, the polyvinylpyrrolidone has a low molecular weight, preferably has a grade varying from K12 to K30. The grades K12, K17 and K25 are particularly preferred.

According to another preferred embodiment, the pore-forming agent is a surfactant, preferably non-ionic, in particular chosen from the group consisting of sodium docusate, potassium docusate, esters of fatty acids and of polyoxyethylene sorbitan (polysorbates), of polyoxygenated hydrogenated castor oil and its derivatives.

According to another preferred embodiment, the swelling agent is polyethylene oxide.

Of course, a person skilled in the art will be able to integrate, as required, one or more additional excipients in the polymer matrix of the compositions according to the invention. For example, these excipients may be antioxidants, antimicrobial preservatives, colorants, plasticizers, lubricants, and/or unmolding agents in the polymer matrix.

A preferred composition of the invention comprises:

- between 35 and 55%, preferably 35% by weight of ethylene-vinyl acetate copolymer,
- between 10 and 30%, preferably 20% by weight of polyethylene glycol, and between 30 and 55%, preferably between 35 and 55%, and even more preferably 45% by weight of progesterone, relative to the total weight of the composition.

An even more preferred composition of the invention comprises:

35% by weight of EVA 40 polymer,

20% by weight of polyethylene glycol having a molecular weight of 4000 g/mol, and 45% by weight of progesterone, relative to the total weight of the composition.

Another preferred composition of the invention comprises:

between 35 and 55%, preferably 55% by weight of ethylene-vinyl acetate copolymer, between 10 and 30%, preferably 15% by weight of polyvinylpyrrolidone, and between 30 and 55%, preferably 30% by weight of progesterone, relative to the total weight of the composition.

The compositions of the invention may further comprise at least one manufacturing aid such as lubricants and plasticizers. Among the lubricants, it is possible to non-exhaustively cite magnesium stearate, talc, colloidal silica, and glyceryl behenate. Among the plasticizers, it is possible to non-exhaustively cite glycerol, triethyl citrate, tributyl citrate, triethyl acetyl citrate, dibutyl sebacate, dibutyl phthalate, tributyl sebacate, glycerol tricaprylate, triacetin, vegetable oils such as castor oil and coconut oil, medium-chain triglycerides, medium-chain polyethylene glycol such as PEG 400, and acetylated monoglycerides. Preferably, the plasticizer may be selected from glycerol, triethyl citrate, tributyl citrate, acetyl triethyl citrate, dibutyl sebacate, triacetin, vegetable oils such as castor oil and coconut oil, medium-chain triglycerides, and acetylated monoglycerides.

The compositions of the invention as defined in the present application can be applied in any type of mammal, preferably a non-human mammal such as a bovine, a sheep, a caprine, an equine, a canine, a feline, and a pig, even more preferably a bovine, a caprine, a sheep, and a pig, advantageously a bovine.

According to a particular embodiment of the invention, the composition is a veterinary composition. Preferably, it is applied to a bovine, and even more preferably to a cow or heifer. According to another particular embodiment, the composition is applied to a caprine, preferably a goat and a ewe, or to a pig, preferably a sow.

According to another particular embodiment of the invention, the composition is applied for several days, preferably at least 3 days, 4 days, 5 days, 6 days, 7 days, 14 days, 18 days, 21 days, and even more preferably, for at least 7 days, 14 days or 18 days.

The compositions according to the invention are specific to the release of progesterone which is, as indicated in the introduction, an active ingredient commonly used in the veterinary field to synchronize estrous in non-human mammals. Preferably, the polymer compositions according to the invention release progesterone mucosally, in particular nasally or intravaginally.

Another subject matter of the invention therefore relates to a use of a composition according to the invention for synchronizing the heats of a group of non-human mammals, preferably a group of bovines, caprines, sheep, or pigs. Preferably, the composition of the invention is administered mucosally, more particularly nasally or intravaginally. The invention therefore also relates to a composition according to the invention for its use to synchronize the estrous of a group of non-human mammals, preferably a group of bovines, caprines, sheep, or pigs.

The invention also relates to a method for synchronizing the estrous of a group of non-human mammals, preferably a group of bovines, caprines, sheep, or pigs, comprising the application of a composition according to the invention, preferably mucosally, more particularly nasally or intravaginally, on said non-human mammals.

An additional object relates to a device with controlled release of progesterone comprising a composition according to the invention. Preferably, the device is a nasal or intravaginal device. Such devices comprise a composition according to the invention having a surface area between 5 and 100 $cm^2$, between 7.5 and 90 $cm^2$, between 10 and 90 $cm^2$, preferably between 15 and 70 $cm^2$, and even more preferably 16 $cm^2$, 20 $cm^2$, 23 $cm^2$25 $cm^2$, 30 $cm^2$, 35 $cm^2$, 40 $cm^2$, 45 $cm^2$, 50 $cm^2$, 60 $cm^2$, and 67 $cm^2$.

Figure 5:
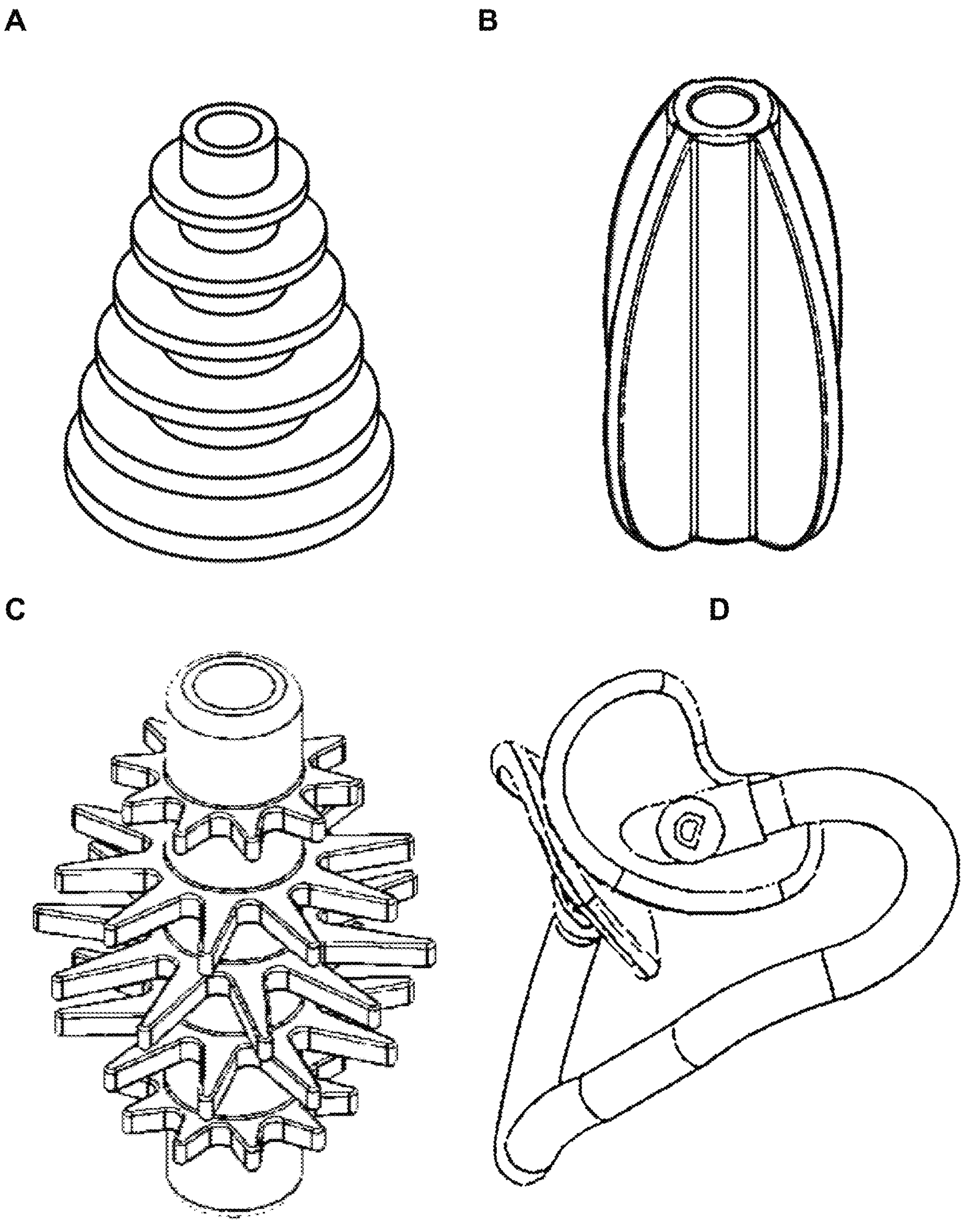

As examples of intravaginal devices, mention may be made of devices in the shape of a hedgehog, Christmas tree or arrow. One particular intravaginal device is a hedgehog-shaped device, as shown in FIG. 5C, comprising a composition according to the invention having a surface area between 10 and 20 $cm^2$, preferably 16 $cm^2$. One particular device is a Christmas tree-shaped device, as shown in FIG. 5A, comprising a composition according to the invention having a surface area between 50 and 80 $cm^2$, preferably 67 $cm^2$. One particular device is an arrow-shaped device, as shown in FIG. 5B, comprising a composition according to the invention having a surface area between 30 and 50 $cm^2$, preferably 40 $cm^2$. Such devices are particularly suitable for application in sows.

One example of a nasal device may be a nose ring. One example of a particular nasal device is a nose ring, as shown in FIG. 5D, comprising a composition according to the invention having a surface area of 60 $cm^2$. Preferentially, the composition of the invention is located at both ends of the nose ring, in particular on the front faces of support plates intended to bear against the nasal septum separating the nostrils of a ruminant. According to a preferred embodiment, the nose ring comprises a composition of the invention having a total surface area of 60 $cm^2$ located at both ends of the nose ring. According to this preferred embodiment, each end of the nose ring comprises a composition of the invention having a surface area of 30 $cm^2$. Such devices are particularly suitable for application in ruminants, preferably bovines.

Other aspects and advantages of the invention will become apparent on reading the following examples, and which must be considered as illustrative and non-limiting.

EXAMPLES

A—Compositions

The compositions of the invention were generally prepared by extrusion followed by injection molding. More particularly, the various ingredients were weighed, manually pre-mixed and then mixed for 30 minutes with a mixer of the Turbula T2F type. The extrusion step was then carried out using the extruder ThermoFisher Pharma 11 Twin-screw. The granulates obtained at the end of the extrusion step were injection-molded so as to obtain a bar-shaped part that was cut to produce parts with a weight of 2 g and of dimensions 47×13×3 mm, corresponding to a surface area of about 16 $cm^2$.

Particular compositions according to the invention are presented in Table 1 below. The comparative compositions of the product Prid delta from the company CEVA Health are also presented by way of illustration.

TABLE 1

| Composition No.: | Thermoplastic polymer (%) | Active ingredient (%) | Pore-forming agent (%) | Swelling agent (%) | Plasticizer (%) |
|---|---|---|---|---|---|
| #4 | Mediprene | Progesterone (50%) | — | — | |
| #5 | EVA 40 (55%) | Progesterone (35%) | PEG 4000 (10%) | — | |
| #6 | EVA 40 (45%) | Progesterone (45%) | PEG 4000 (10%) | — | |
| #7 | EVA 40 (40%) | Progesterone (35%) | PEG 4000 (20%) | — | |
| #8 | EVA 40 (35%) | Progesterone (45%) | PEG 4000 (20%) | — | |
| #9 | EVA 40 (35%) | Progesterone (35%) | PEG 4000 (30%) | — | |
| #10 | EVA 40 (35%) | Progesterone (55%) | PEG 4000 (10%) | — | |
| #11 | EVA 40 (40%) | Progesterone (50%) | PEG 3350 (10%) | — | |
| #12 | EVA 40 (40%) | Progesterone (40%) | PEG 3350 (20%) | — | |
| #13 | EVA 28 (40%) | Progesterone (50%) | PEG 3350 (10%) | — | |
| #14 | EVA 40 (40%) | Progesterone (50%) | — | PEO 8000000 (10%) | |
| #15 | EVA 40 (40%) | Progesterone (50%) | — | PEO 1000000 (10%) | |
| #16 | EVA 28 (40%) | Progesterone (50%) | — | PEO 8000000 (10%) | |
| #17 | EVA 40 (35%) | Progesterone (50%) | PEG 4000 (15%) | | |
| #18 | EVA 40 (37%) | Progesterone (45%) | PEG 3350 (18%) | | |
| #19 | EVA 40 (55%) | Progesterone (30%) | PVP K12 (15%) | | |
| #20 | EVA 40 (45%) | Progesterone (35%) | Sodium docusate (10%) | | PEG 400 (10%) |
| #21 | EVA 40 (50%) | Progesterone (30%) | polyoxyoxidized hydrogenated castor oil 40 (10%) | | triacetin (10%) |
| Prid delta | EVA 18 (89%) | Progesterone (11%) | — | — | |

%: The percentages are expressed by weight relative to the total weight of the composition.
EVA: Ethylene-vinyl acetate
TPE-U: Polyurethane thermoplastic elastomer polymer
PEG: Polyethylene glycol
PEO: Polyethylene oxide

B—Amount of Progesterone Released by the Compositions of the Invention

The amount of progesterone released by the compositions of the invention is measured according to the DISSOLUTEST method using a type 2 apparatus (paddle apparatus) described in the European, American, and Japanese pharmacopoeia.

The results are presented in Table 2 below.

TABLE 2

| | Composition No.: | | | | | | | |
|---|---|---|---|---|---|---|---|---|
| Time (H) | #4 Q. (mg) | #5 Q. (mg) | #6 Q. (mg) | #7 Q. (mg) | #8 Q. (mg) | #9 Q. (mg) | #10 Q. (mg) | #17 Q. (mg) |
| 0 | 0 | 0 | 0 | 0 | 0 | 0 | 0 | 0 |
| 1 | ND | 15 | 18 | 22 | 26 | 25 | 26 | 23 |
| 3 | 50 | 26 | 33 | 41 | 48 | 47 | 49 | 43 |
| 6 | 69 | 20 | 48 | 60 | 70 | 68 | 73 | 64 |
| 24 | 130 | 79 | 103 | 127 | 149 | 143 | 159 | 137 |
| 48 | 178 | 113 | 152 | 183 | 216 | 203 | 231 | 199 |
| 96 | 241 | 1162 | 222 | 260 | 312 | 288 | 330 | 288 |
| 144 | 288 | 196 | 275 | 317 | 382 | 345 | 402 | 354 |
| 168 | ND | 211 | 298 | 340 | 411 | 372 | 430 | 382 |

Q.: Amount of progesterone released in mg
ND: Not determined

Comparative results between the amount of progesterone per unit of surface area released by composition #8 and Prid delta are shown in FIG. 1.

C—Progesterone Diffusion Profile

The progesterone diffusion rate obtained using the compositions of the invention is calculated according to the following equation:

$$\text{Dif. } r. (\%) = (Q_{,released} \text{ of progesterone in composition (mg)}/Q_{,initial} \text{ of progesterone in the medium}) \times 100$$

The progesterone diffusion rate obtained using the compositions of the invention is determined according to the method described above.

The results are presented in Table 3 below and are illustrated by FIGS. 2-4.

TABLE 3

| | Composition No.: | | | | | | | | |
|---|---|---|---|---|---|---|---|---|---|
| Sampling time (H) | #4 Dif. r. (%) | #8 Dif. r. (%) | #9 Dif. r. (%) | #10 Dif. r. (%) | #11 Dif. r. (%) | #12 Dif. r. (%) | #14 Dif. r. (%) | #15 Dif. r. (%) | #18 Dif. r. (%) |
| 0 | 0 | 0 | 0 | 0 | 0 | 0 | 0 | 0 | 0 |
| 3 | 4.6 | 5.3 | 6.6 | 4.3 | 4.3 | 6 | 4.2 | 3.9 | 5.4 |
| 6 | 6.2 | 7.8 | 9.6 | 6.4 | 6.5 | 8.6 | 5.8 | 5.5 | 8.2 |
| 24 | 11.3 | 16.5 | 19.8 | 13.9 | 14.4 | 16.8 | 10.7 | 10.8 | 18.7 |
| 48 | 15.1 | 24.0 | 28.3 | 20.2 | 20.7 | 23.2 | 14.4 | 15.2 | 27.6 |
| 96 | 20.2 | 34.6 | 40.1 | 29.1 | 29.5 | 31.2 | 19.4 | 21.3 | 39.0 |
| 144 | 23.6 | 42.4 | 47.3 | 35.6 | 35.9 | 38.0 | 23.2 | 25.7 | 46.6 |
| 168 | 25 | 45.6 | 51.7 | 38.2 | 38.5 | ND | ND | 27.6 | 49.6 |

Dif. r.: Progesterone diffusion rate (%)
ND: Not determined

D—Hardness of the Compositions of the Invention

The hardness of the compositions of the invention is measured by a type A durometer according to standard ASTM D2240. The results are presented in Table 4 below.

TABLE 4

| Composition No.: | Shore A Hardness |
|---|---|
| #3B | 90 |
| #4 | 78 |
| #11 | 62 |
| #12 | 64 |
| #13 | 93 |
| #14 | 63 |
| #16 | 93 |

E—Conclusions

The results show that the polymer compositions according to the invention concentrated with progesterone (between 30 and 55%, preferably between 35 and 55% by weight relative to the total weight of the composition) have progesterone diffusion rates substantially comparable to the polymer composition Prid delta, although less concentrated with progesterone (11% by weight), in particular for the compositions of the invention further comprising polyethylene glycol.

The results of Table 4 show a certain flexibility of the polymer compositions of the invention, in particular for the compositions of the invention further comprising polyethylene glycol.

In conclusion, the inventors have demonstrated that the polymer compositions of the invention concentrated with progesterone (between 30 and 55% by weight relative to the total weight of the composition) made it possible to release and deliver progesterone in an extended, continuous manner in an amount sufficient to achieve the desired therapeutic objective. The polymer compositions of the invention concentrated with progesterone are relatively flexible and can thus be used in smaller and more compact administration devices, which are therefore more comfortable for the mammal.

The invention claimed is:

1. A composition comprising:
between 35 and 55% by weight of a polymer matrix comprising a thermoplastic polymer having a Shore A hardness of between 20 and 100 as measured by a Type A durometer according to the ASTM D2240 standard and a melting point of between 40 and 200° C.; and
between 30 and 55% by weight of progesterone,
relative to the total weight of the composition.

2. A composition comprising:
a polymer matrix comprising a thermoplastic polymer having a Shore A hardness of between 20 and 100 as measured by a Type A durometer according to the ASTM D2240 standard and a melting point of between 4° and 200° C.; and
progesterone,
wherein the ratio by weight of progesterone to the polymer matrix is between 0.5 and 2.

3. A composition comprising:
a polymer matrix comprising a thermoplastic polymer having a Shore A hardness of between 20 and 100 as measured by a Type A durometer according to the ASTM D2240 standard and a melting point of between 40 and 200° C.; and
progesterone,
wherein the area density of progesterone in the polymer matrix is between 20 and 100 mg/cm$^2$.

4. The composition according to claim 1, wherein said thermoplastic polymer is chosen from a thermoplastic polymer of the EVA type, and a thermoplastic elastomer polymer (TPE).

5. The composition according to claim 4, wherein the thermoplastic polymer of the EVA type is an ethylene-vinyl acetate copolymer comprising 18%, 28%, or 40% by weight of vinyl acetate monomer relative to the total weight of ethylene-vinyl acetate copolymer.

6. The composition according to claim 4, wherein the thermoplastic elastomer polymer (TPE) is selected from a styrene block-based thermoplastic elastomer polymer (TPE-S), and a polyurethane thermoplastic elastomer polymer (TPE-U).

7. The composition according to claim 4, wherein the thermoplastic elastomer polymer (TPE) is a styrene block-based thermoplastic elastomer polymer (TPE-S) chosen from a block copolymer of polystyrene-polybutadiene-polystyrene (SBS), a block copolymer of polystyrene-polyisoprene-polystyrene (SIS), a block copolymer of polystyrene-polyisobutylene-polystyrene (SIBS), a block copolymer of polystyrene-poly(ethylene-propylene)-polystyrene (SEPS), a block copolymer of polystyrene-poly(ethylene-propylene) (SEP), a block copolymer of polystyrene-poly(ethylene-butylene)-polystyrene (SEBS), a block copolymer of poly-α-methylstyrene-poly(butadiene-isoprene)-α-methylstyrene, a block copolymer of polydimethylsiloxane-styrene, a graft block copolymer of polystyrene-polybutadiene, a graft block copolymer of polystyrene-poly(ethylene oxide), a block copolymer of poly[styrene-per-dimethylsiloxane), and a block copolymer of polyisobutylene polystyrene (PIB-PS).

8. The composition according to claim 4, wherein the thermoplastic elastomer polymer (TPE) is a formulation comprising a block copolymer of polystyrene-poly(ethylene-butylene)-polystyrene (SEBS), paraffin oil, and polypropylene.

9. The composition according to claim 1, wherein the composition further comprises between 5 and 35% by weight of a pore-forming agent and/or a swelling agent, relative to the total weight of the composition.

10. The composition according to claim 9, wherein the pore-forming agent is polyethylene glycol, having preferably a molecular weight between 1500 and 8000 g/mol.

11. The composition according to claim 9, wherein the swelling agent is polyethylene oxide.

12. The composition according to claim 1, wherein the composition comprises:

between 35 and 55% by weight of ethylene-vinyl acetate copolymer, between 10 and 30% by weight of polyethylene glycol, and between 30 and 55% by weight of progesterone, relative to the total weight of the composition.

13. The composition according to claim 1, wherein the composition comprises:

between 35 and 55% by weight of a formulation comprising a polystyrene-poly(ethylene-butylene)-polystyrene block copolymer, paraffin oil, and polypropylene; and between 30 and 55% by weight of progesterone, relative to the total weight of the composition.

14. The composition as defined according to claim 1, wherein the composition is a veterinary composition, said composition being applied to a bovine, a caprine, a sheep, and a pig.

15. A method for synchronizing the estrous of a group of non-human mammals, comprising applying a composition as defined according to claim 1 to the non-human mammals.

16. The method according to claim 15, wherein the composition is applied mucosally.

17. A device with controlled release of progesterone comprising a composition according to claim 1.

18. The device according to claim 17, wherein the device is a nasal device.

19. The device according to claim 17, wherein the device is an intravaginal device.

20. The method according to claim 15, wherein the group of non-human mammals is a group of bovines, caprines, sheep or pigs.

* * * * *